United States Patent
Momose et al.

(10) Patent No.: US 11,714,057 B2
(45) Date of Patent: Aug. 1, 2023

(54) METHOD OF MANUFACTURING GAS SENSOR DEVICE

(71) Applicant: FUJITSU LIMITED, Kawasaki (JP)

(72) Inventors: Satoru Momose, Atsugi (JP); Michio Ushigome, Atsugi (JP); Kazuaki Karasawa, Hadano (JP); Osamu Tsuboi, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 72 days.

(21) Appl. No.: 17/327,825

(22) Filed: May 24, 2021

(65) Prior Publication Data

US 2021/0278357 A1 Sep. 9, 2021

Related U.S. Application Data

(62) Division of application No. 15/957,977, filed on Apr. 20, 2018, now abandoned.

(30) Foreign Application Priority Data

Apr. 28, 2017 (JP) .................... 2017-090084

(51) Int. Cl.
*G01N 27/12* (2006.01)
*G01N 33/84* (2006.01)
*G01N 33/497* (2006.01)

(52) U.S. Cl.
CPC ......... *G01N 27/125* (2013.01); *G01N 33/497* (2013.01); *G01N 33/84* (2013.01); *G01N 2033/4975* (2013.01)

(58) Field of Classification Search
CPC .... G01N 27/125; G01N 33/497; G01N 33/84; G01N 2033/4975; G01N 27/4141
See application file for complete search history.

(56) References Cited

U.S. PATENT DOCUMENTS

| | | | |
|---|---|---|---|
| 2008/0221806 A1 | 9/2008 | Bryant et al. | |
| 2009/0275852 A1 | 11/2009 | Oki et al. | |
| 2010/0005852 A1 | 1/2010 | McMurtry et al. | |
| 2010/0005858 A1* | 1/2010 | Virji ................ | G01N 27/127 73/31.05 |
| 2015/0096610 A1 | 4/2015 | Okubo et al. | |

FOREIGN PATENT DOCUMENTS

| | | |
|---|---|---|
| JP | H11-23508 A | 1/1939 |
| JP | H11-23508 A | 1/1999 |

(Continued)

OTHER PUBLICATIONS

Hong et al, Single-Step Preparation of Polythiophene Bearing Branched Chains by Dual Initiation Polymerization, 2017, Macromolecular Research, 25, pp. 243-248 (Year: 2017).*

(Continued)

*Primary Examiner* — Matthew D Krcha
*Assistant Examiner* — Austin Q Le
(74) *Attorney, Agent, or Firm* — Fujitsu Patent Center

(57) ABSTRACT

A gas sensor device includes a first electrode, a second electrode, and a polythiophene film which is formed between the first and second electrodes to be electrically coupled to the first and second electrodes, and to which cuprous bromide is adsorbed.

2 Claims, 20 Drawing Sheets

(56) References Cited

FOREIGN PATENT DOCUMENTS

| | | | |
|---|---|---|---|
| JP | H11-72453 A | 3/1999 | |
| RU | 2606231 C1 * | 1/2017 | ......... C08G 73/0266 |

OTHER PUBLICATIONS

Virji et al, Polyaniline Nanofiber Composites with Metal Salts: Chemical Sensors for Hydrogen Sulfide, 2005, Small, vol. 1, issue 6, 624-627 (Year: 2005).*

P. Lauque et al., "Highly sensitive and selective room temperature NH3 gas microsensor using an ionic conductor (CuBr) film", Analytica Chimica Acta vol. 515 (2004) pp. 279-284, May 25, 2004 (6 pages).

Zhang et al, Enhancing σ/π-type copper(I)—thiophene interactions by metal doping (metal=Li, Na, K, Ca, Sc), Oct. 2014, Dalton Transactions, vol. 44, Issue 3, pp. 1283-1281 (Year: 2014).

Zhao, "Impraving ths Conductivity of PEDOT: PSS Hole Transport Layer in Polymer Solar Cells vie Copper (II) Bromide Salt Doping", ACS Applied Materials & Interfaces, Dec. 2015, 7, 3, pp. 1439-1448 (Year: 2015).

USPTO, (LE) Final Rejection, dated Feb. 9, 2021, in parent U.S. Appl. No. 15/957,977 [pending].

USPTO, (LE) Non-Final Rejection, dated Oct. 20, 2020 in parent U.S. Appl. No. 15/957,977 [pending].

USPTO, (LE) Non-Final Rejection, dated Jun. 23. 2020, in parent U.S. Appl. No. 15/957,977 [pending].

USPTO, (LE) Restriction/Election Requirement, dated Mar. 6, 2020, in parent U.S. Appl. No. 15/957,977 [pending].

Zhang et al, Enhancing σ/π-type copper(I)—thiophene interactions by metal doping (metal=Li, Na, K, Ca, Sc), Oct. 2014, Dalton Transactions, vol. 44, Issue 3, pp. 1283-1291 (Year: 2014).

USPTO, (LE) Non-Final Rejection, dated Oct. 20, 2020. in parent U.S. Appl. No. 15/967,977 [pending].

* cited by examiner

METHOD OF MANUFACTURING GAS SENSOR DEVICE

CROSS-REFERENCE TO RELATED APPLICATION

This application is a divisional of application Ser. No. 15/957,977, filed Apr. 20, 2018, which is based upon and claims the benefit of priority of the prior Japanese Patent Application No. 2017-090084, filed on Apr. 28, 2017, the entire contents of which are incorporated herein by reference.

FIELD

The embodiments discussed herein are related to a gas sensor device, a gas measuring device, and a method of manufacturing a gas sensor device.

BACKGROUND

Research and development are being conducted to discover a disease at an early stage before a self-perceived symptom is manifested, by detecting a specific chemical substance contained in the exhaled breath of a person. There has been known a gas sensor device which detects a detection target gas, by using the phenomenon that when a contacting portion of a semiconductor formed on an electrode is exposed to a measurement target gas, the electric resistance value of the contacting portion changes due to the contact of the detection target gas. By using the gas sensor device, a simple examination may be performed to detect a gas indicating an occurrence of a disease from gases contained in the exhaled breath.

In order to detect a specific detection target gas from the measurement target gas in which a plurality of gases is mixed with each other, a gas sensor device exhibiting a high gas species selectivity is used. For example, the gas sensor device may exhibit a response by a change of an electric resistance value with respect to the detection target gas at a rate of about 100 or more times over another gas (other than the detection target gas) contained in the measurement target gas. For example, a gas sensor device using cuprous bromide is known as a gas sensor device exhibiting a high ammonia gas selectivity.

Related technologies are disclosed in, for example, Analytica Chimica Acta Vol. 515 (2004), p. 279-284.

SUMMARY

According to an aspect of the embodiments, a gas sensor device includes a first electrode, a second electrode, and a polythiophene film which is formed between the first and second electrodes to be electrically coupled to the first and second electrodes, and to which cuprous bromide is adsorbed.

The object and advantages of the disclosure will be realized and attained by means of the elements and combinations particularly pointed out in the claims. It is to be understood that both the foregoing general description and the following detailed description are exemplary and explanatory and are not restrictive of the disclosure, as claimed.

DESCRIPTION OF EMBODIMENTS

Figure 1:
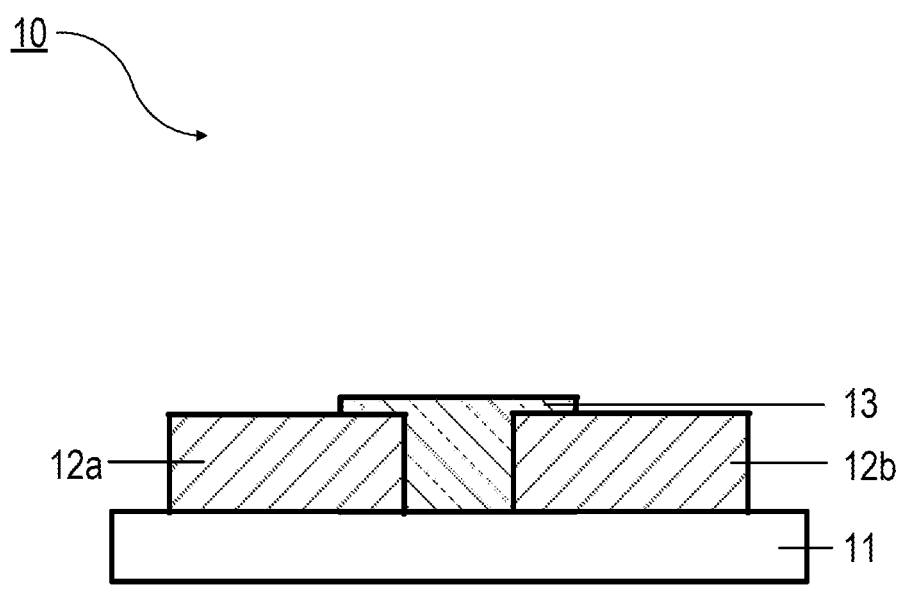
FIG. 1 is a sectional view of a gas sensor device according to a first embodiment.

Among the non-detecting gases contained in the measurement target gas, there is a gas which comes into contact with the contacting portion like the detection target gas and changes an electric resistance value of the contacting portion although the change is small as compared with the detection target gas. Due to the non-detecting gases contacting the contacting portion to change the electric resistance value, the detection target gas selectivity of the gas sensor device decreases, and thus, an accurate quantification of the detection target gas may not be performed.

Hereinafter, a gas sensor device, a gas measuring device, and a method of manufacturing the gas sensor device according to embodiments of the present disclosure will be described with reference to FIGS. 1 to 20. The scope of the technology of the present disclosure is not limited to the embodiments and includes the matters defined in the claims and equivalents thereto. Further, components corresponding to each other in different drawings will be denoted by the same reference numeral, and overlapping descriptions thereof will be omitted.

Hereinafter, a gas sensor device according to a first embodiment will be described with reference to FIGS. 1 to 6. The gas sensor device according to the first embodiment exhibits a response by a change of an electric resistance value with respect to a contact of a detection target gas contained in a measurement target gas. In the gas sensor device according to the first embodiment, the measurement target gas is, for example, the exhaled breath of a person, and the detection target gas is ammonia gas.

Figure 2:
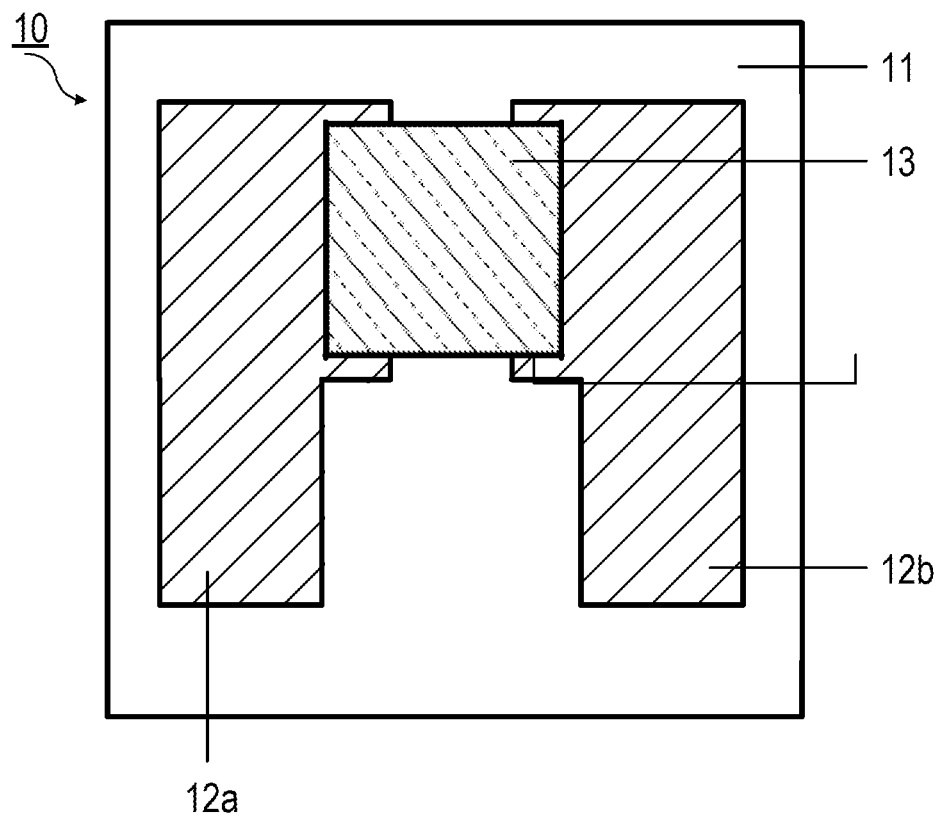
FIG. 2 is a top view of the gas sensor device according to the first embodiment.

FIG. 1 is a sectional view of the gas sensor device according to the first embodiment. FIG. 2 is a top view of the gas sensor device according to the first embodiment. As illustrated in FIGS. 1 and 2, a gas sensor device 10 includes a substrate 11, two electrodes 12a and 12b, and a contacting portion 13.

The substrate 11 is, for example, a silicon wafer with a thermal oxide film formed thereon (e.g., the length of the thermal oxide film is 100 nm) and having a side of 15 mm.

The two electrodes 12a and 12b are provided as a first electrode 12a and a second electrode 12b on the substrate 11. For example, each of the two electrodes 12a and 12b has a width of 5 mm, a length of 6 mm, and a film thickness of 60 nm. The two electrodes 12a and 12b are arranged at a predetermined interval therebetween, for example, an interval of 1 mm.

The contacting portion 13 is electrically coupled to the two electrodes 12a and 12b, and is a polythiophene film 14 with cuprous bromide adsorbed thereto. The contacting portion 13 has, for example, a rectangular shape having a film thickness of 60 nm and a side of 5 mm.

The polythiophene film 14 is composed of a plurality of polythiophene molecules and may have a stacking structure in which thiophene rings of the plurality of polythiophene molecules are stacked in the direction from the first electrode 12a toward the second electrode 12b, in view of detecting the detection target gas with a high response sensitivity when detecting the detection target gas by using the gas sensor device 10. The plurality of respective polythiophene molecules may be stacked in a state of being inclined with respect to the direction from the first electrode 12a toward the second electrode 12b.

The polythiophene film 14 may have polythiophene with a high conductivity as a p-type semiconductor, in view of detecting the detection target gas with a high response sensitivity when detecting the detection target gas by using the gas sensor device 10. A specific material for the polythiophene of the polythiophene film 14 is, for example, poly(3-hexylthiophene) (PH3T).

For example, cuprous bromide may be physically adsorbed to the polythiophene film 14 and be present in a distance in which exchange of electrons with the polythiophene molecules of the polythiophene film 14 may be performed. For example, cuprous bromide may be chemically adsorbed to the polythiophene film 14 through a coordination bond formation and form coordination bonds with the polythiophene molecules of the polythiophene film 14. The cuprous bromide has copper (I) ions and bromide ions.

Figure 3:
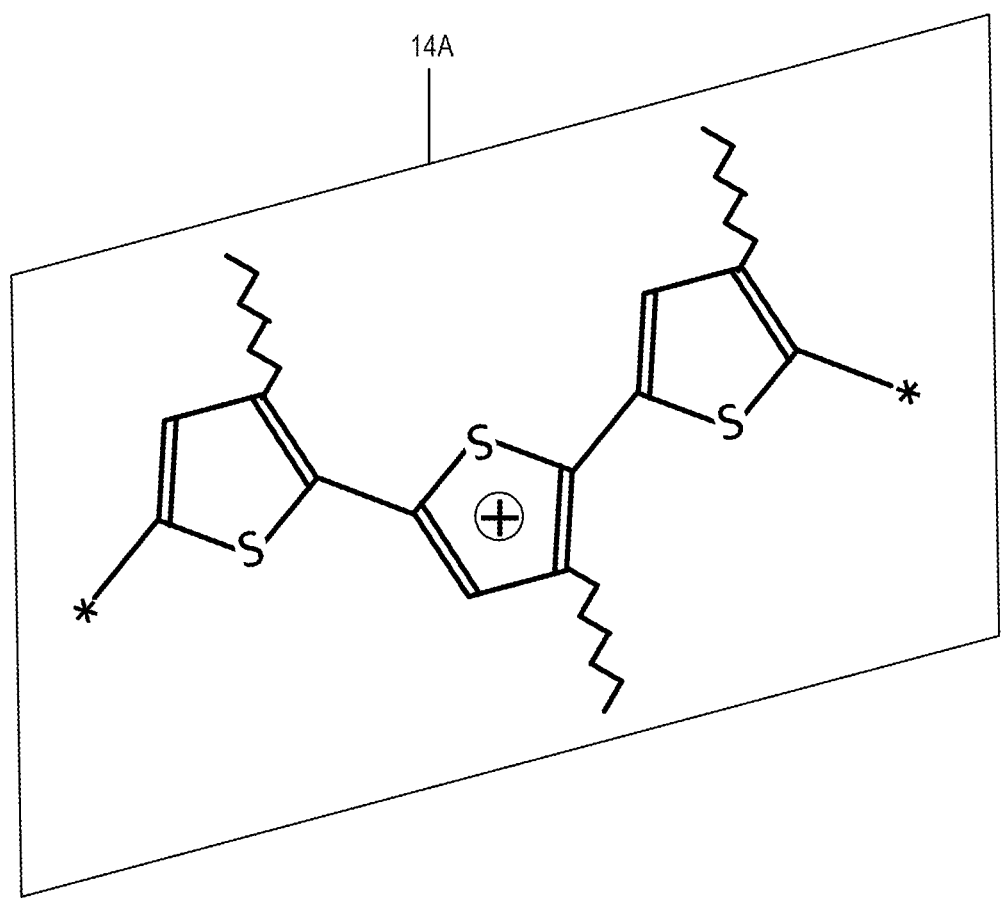
FIG. 3 is a view illustrating a polythiophene plane of the gas sensor device according to the first embodiment.

FIG. 3 is a view illustrating a polythiophene plane of the gas sensor device according to the first embodiment. As illustrated in FIG. 3, the polythiophene film 14 has repeating units of polythiophene which include thiophene rings. The atoms constituting the thiophene rings included in the repeating units of polythiophene are present on the same plane 14A (a polythiophene plane 14A).

Figure 4:
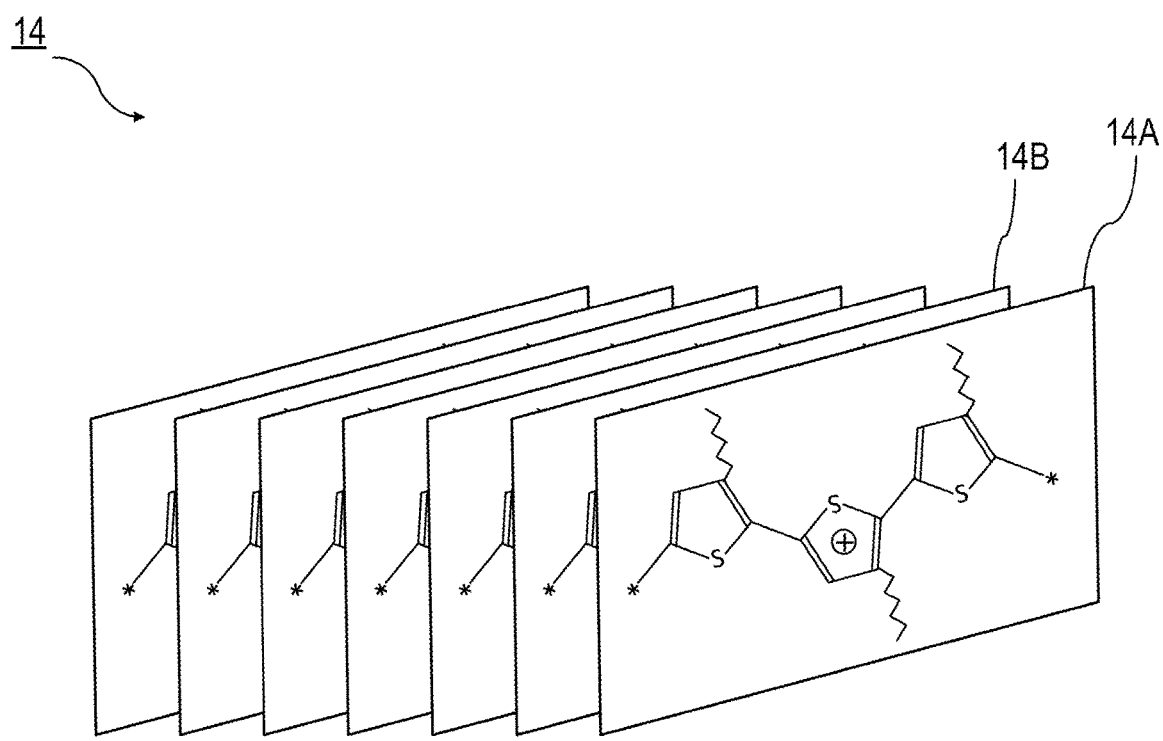
FIG. 4 is a view illustrating a stacking structure of polythiophene in the gas sensor device according to the first embodiment.

FIG. 4 is a view illustrating a stacking structure of polythiophene in the gas sensor device according to the first embodiment. As illustrated in FIG. 4, the polythiophene film 14 may have a plurality of polythiophene molecules having a stacking structure in which the polythiophene plane 14A and other polythiophene planes including a polythiophene plane 14B are superimposed on each other. The plurality of polythiophene molecules become stable in the stacking structure by a n-n interaction.

The cuprous bromide is adsorbed to the lateral portions of the polythiophene in the stacking structure. When the cuprous bromide is adsorbed to the lateral portions of the polythiophene in the stacking structure, the cuprous bromide is exposed to the vicinity of the surface of the contacting portion 13. Since the detection target gas easily comes into contact with the cuprous bromide, the gas sensor device 10 exhibits a high response sensitivity to the detection target gas.

As described above, the gas sensor device 10 includes the contacting portion 13 which is the polythiophene film 14 with cuprous bromide adsorbed thereto, so that the gas sensor device 10 exhibits a response by a change of an electric resistance value with respect to a contact of the ammonia gas which is the detection target gas with a high sensitivity, and exhibits a response by a change of an electric resistance value with respect to a contact of the hydrogen sulfide gas which is a gas other than the detection target gas with a low sensitivity. Thus, the gas sensor device 10 exhibits a high ammonia gas selectivity.

Hereinafter, an estimated operation principle of the gas sensor device according to the first embodiment will be described with reference to FIGS. 5 and 6.

Figure 5:
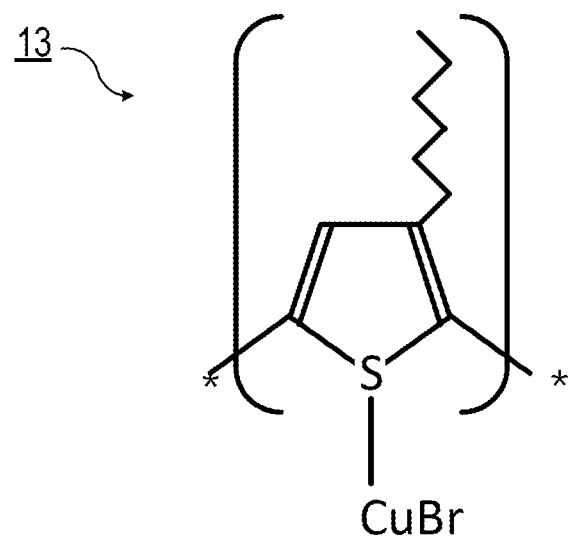
FIG. 5 is a view illustrating a molecular structure of a contacting portion of the gas sensor device according to the first embodiment.

FIG. 5 is a view illustrating a molecular structure of the contacting portion of the gas sensor device according to the first embodiment. The cuprous bromide and the polythiophene form a coordination bond in the manner that a sulfur atom of a thiophene ring included in the polythiophene donates an electron to the cuprous bromide.

Figure 6:
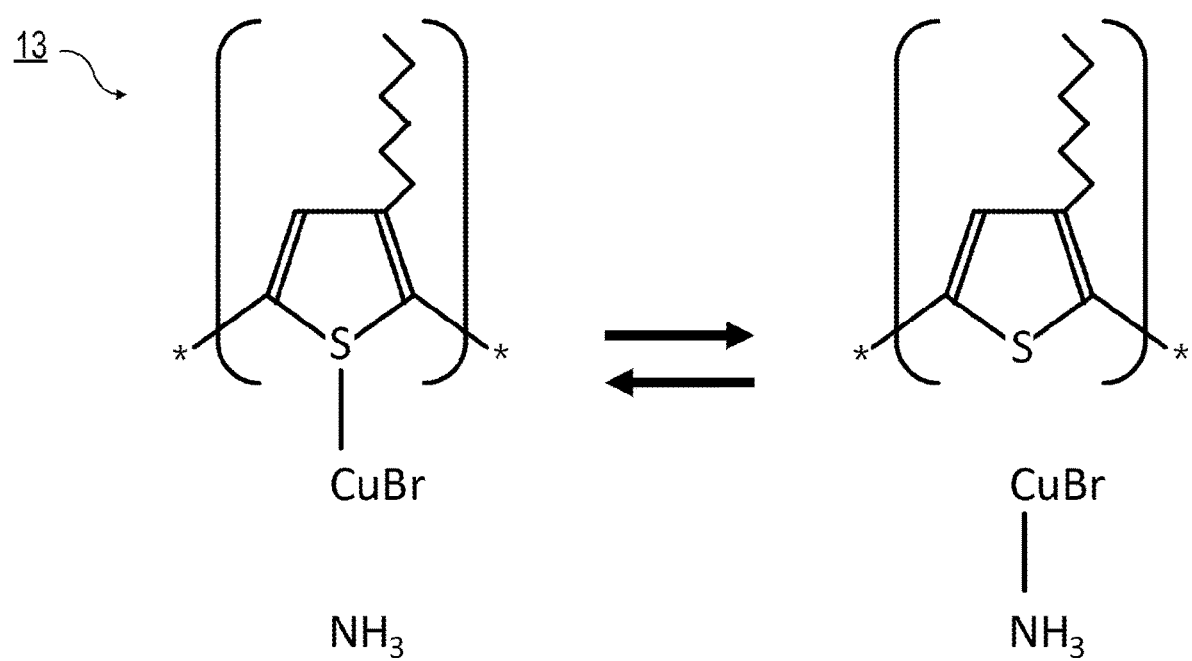
FIG. 6 is a view illustrating an estimated equilibrium state of molecules in the contacting portion when the contacting portion comes into contact with a gas, in the gas sensor device according to the first embodiment.

FIG. 6 is a view illustrating an estimated equilibrium state of molecules in the contacting portion when the contacting portion comes into contact with a gas, in the gas sensor device according to the first embodiment. When ammonia which is the detection target gas approaches and comes into contact with the contacting portion 13, the ammonia forms a coordination bond by donating an electron to the cuprous bromide. When the coordination bond between the ammonia and the cuprous bromide is formed, the coordination bond between the polythiophene and the cuprous bromide is decoupled.

When the coordination bond between the polythiophene and the cuprous bromide is decoupled, the electron that has been donated to the cuprous bromide is returned to the polythiophene film 14. Since the concentration of a p-type carrier of the polythiophene film 14 decreases, the electric resistance value of the contacting portion 13 increases.

When the concentration of the ammonia in the measurement target gas exposed to the contacting portion 13 increases, the coordination bond between the ammonia and the cuprous bromide is formed as indicated by the rightward arrow in FIG. 6. To the contrary, when the concentration of the ammonia in the measurement target gas exposed to the contacting portion 13 decreases, the coordination bond between the polythiophene and the cuprous bromide is formed as indicated by the leftward arrow in FIG. 6.

Depending on the concentration of ammonia in the measurement target gas to be exposed, a reaction shifts from the equilibrium state of molecules to the formation of the coordination bond on the contacting portion 13, thereby changing the rate of the formation of the coordination bond between the ammonia and the cuprous bromide, so that the gas sensor device 10 exhibits a response by the change of the electric resistance value.

Since the ability of ammonia to form a coordination bond with the cuprous bromide is much higher than the ability of polythiophene to form a coordination bond with the cuprous bromide, the coordination bond between the polythiophene and the cuprous bromide is immediately decoupled, and the coordination bond between the ammonia and the cuprous bromide is formed, on the contacting portion 13 exposed to the ammonia gas. Since the speed for forming the coordination bond between the ammonia and the cuprous bromide immediately increases in the gas sensor device 10 exposed to the ammonia gas, the gas sensor device 10 exhibits the response by the change of the electric resistance value with a high sensitivity.

Meanwhile, since the ability of hydrogen sulfide to form a coordination bond with cuprous bromide is equal to the ability of polythiophene to form a coordination bond with cuprous bromide, it takes longer to disconnect the coordination bond between the polythiophene and the cuprous bromide on the contacting portion 13 exposed to the hydrogen sulfide gas, than decoupling the coordination bond between the polythiophene and the cuprous bromide on the contacting portion 13 exposed to the ammonia gas. Since the speed for forming the coordination bond between the hydrogen sulfide and the cuprous bromide hardly increases due to the hindrance by the coordination bond between the polythiophene and the cuprous bromide, the gas sensor device 10 exposed to the hydrogen sulfide exhibits the response by the change of the electric resistance value with a low sensitivity.

Hereinafter, a method of manufacturing the gas sensor device according to the first embodiment will be described with reference to FIGS. 7 to 10.

The method of manufacturing the gas sensor device according to the first embodiment forms the first and second electrodes on the substrate, forms the polythiophene film to be electrically coupled to the first and second electrodes, and brings cupric bromide into contact with the polythiophene film so as to form the contacting portion which is the polythiophene film with cuprous bromide adsorbed thereto.

Figure 7:
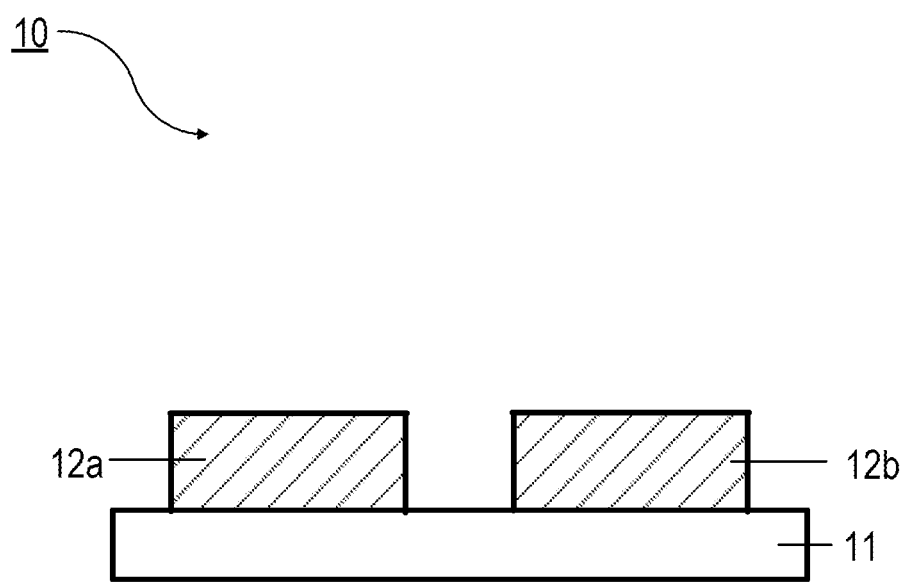
FIG. 7 is a view illustrating a process of a method of manufacturing the gas sensor device according to the first embodiment.

FIG. 7 is a view illustrating a process of the method of manufacturing the gas sensor device according to the first embodiment. As illustrated in FIG. 7, the two electrodes 12a and 12b are formed on the substrate 11. The substrate 11 is, for example, a silicon wafer with a thermal oxide film formed thereon (e.g., the length of the thermal oxide film is 100 nm) and having a side of 15 mm. The two electrodes 12a and 12b are gold electrodes each having a width of 5 mm, a length of 6 mm, and a film thickness of 60 nm, and are formed at an interval of 1 mm therebetween by using vacuum deposition.

Figure 8:
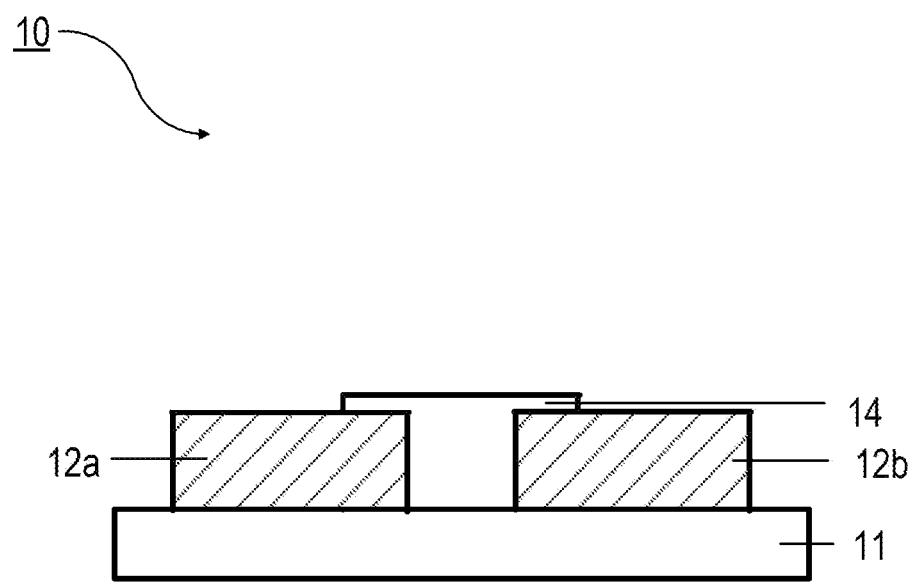
FIG. 8 is a view illustrating a process of the method of manufacturing the gas sensor device according to the first embodiment.

FIG. 8 is a view illustrating a process of the method of manufacturing the gas sensor device according to the first embodiment. The polythiophene film 14 is formed to be electrically coupled to the two electrodes 12a and 12b. The polythiophene film 14 may be formed by, for example, a method of applying 1 μL of P3HT solution dissolved in o-dichlorobenzene at a concentration of 1% by weight into a rectangular shape having a side of 5 mm, and performing a natural drying, in view of increasing the yield of the polythiophene film 14 having the high conductivity and obtaining the gas sensor device capable of detecting the detection target gas with a high response sensitivity.

Figure 9:
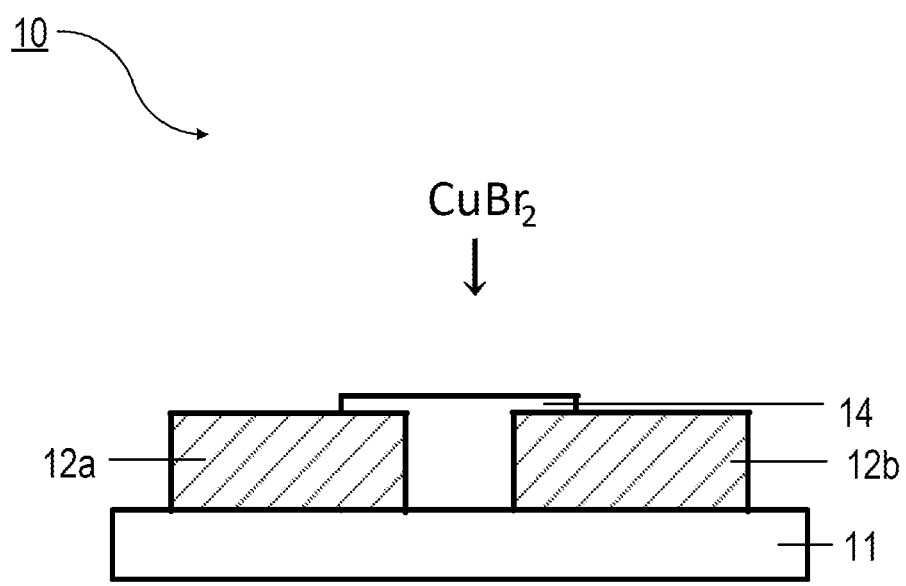
FIG. 9 is a view illustrating a process of the method of manufacturing the gas sensor device according to the first embodiment.

FIG. 9 is a view illustrating a process of the method of manufacturing the gas sensor device according to the first embodiment. Cupric bromide is brought into contact with the polythiophene film 14. In order to bring the cupric bromide into contact with the polythiophene film 14, for example, a methanol solution in which the concentration of the cupric bromide is 0.1 mol/L is dropped and left standing for 5 minutes, and then, washing with pure methanol and natural drying are performed.

Copper (II) ions contained in the cupric bromide oxidize the polythiophene film 14 to receive the electrons of the polythiophene film 14 and be reduced into copper (I) ions. Cuprous bromide is formed by the oxidation-reduction reaction and adsorbed to the polythiophene film 14.

Figure 10:
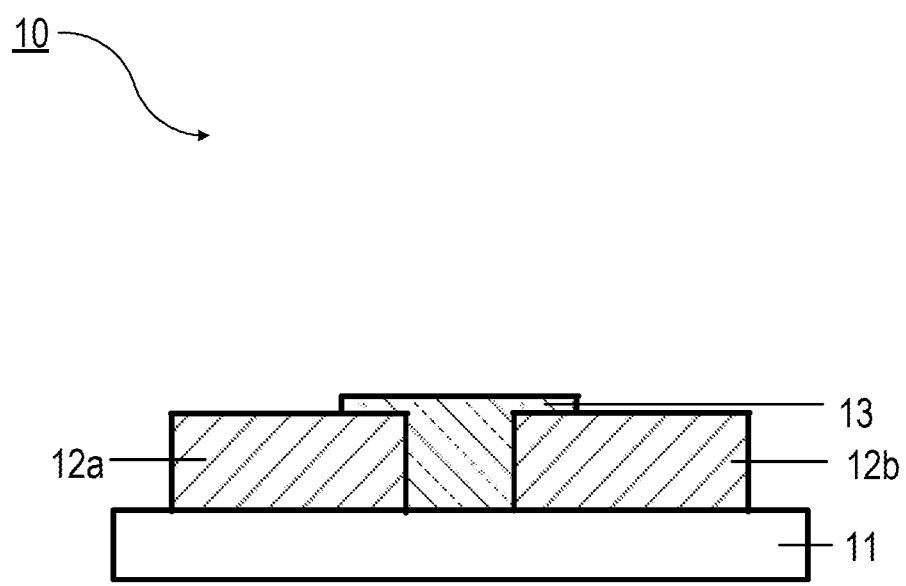
FIG. 10 is a view illustrating a process of the method of manufacturing the gas sensor device according to the first embodiment.

FIG. 10 is a view illustrating a process of the method of manufacturing the gas sensor device according to the first embodiment. As illustrated in FIG. 10, the contacting portion 13 which is the polythiophene film 14 with cuprous bromide adsorbed thereto is formed so that the gas sensor device 10 is manufactured.

As described above, the method of manufacturing the gas sensor device forms the contacting portion 13 electrically coupled to the first electrode 12a and the second electrode 12b and corresponding to the polythiophene film 14 with cuprous bromide adsorbed thereto, so that the gas sensor device 10 having an improved ammonia gas selectivity may be manufactured.

An element analysis by the X-ray photoelectron spectroscopy (XPS) is performed on the gas sensor device 10 manufactured by the method of manufacturing the gas sensor device according to the first embodiment. When an element composition ratio analysis by the XPS is performed on the surface of the polythiophene film 14 with cuprous bromide adsorbed thereto in an analyte depth of about 5 nm, the ratio of the number of copper atoms, the number of bromine atoms, the number of sulfur atoms, and the number of carbon atoms is about 1:1:13:130.

The analyte depth is about 5 nm with respect to the 60 nm film thickness of the polythiophene film 14, and in view of the ratio of the number of the carbon atoms and the number of the sulfur atoms, the surface of the polythiophene film 14 contains one copper atom per 13 thiophene rings. In addition, the observed copper atoms are in the ionic state, and it is estimated that the ratio between monovalent ions and divalent ions is about 10:1. Thus, most of the copper compounds adsorbed to the polythiophene film 14 are cuprous bromide.

Figure 11:
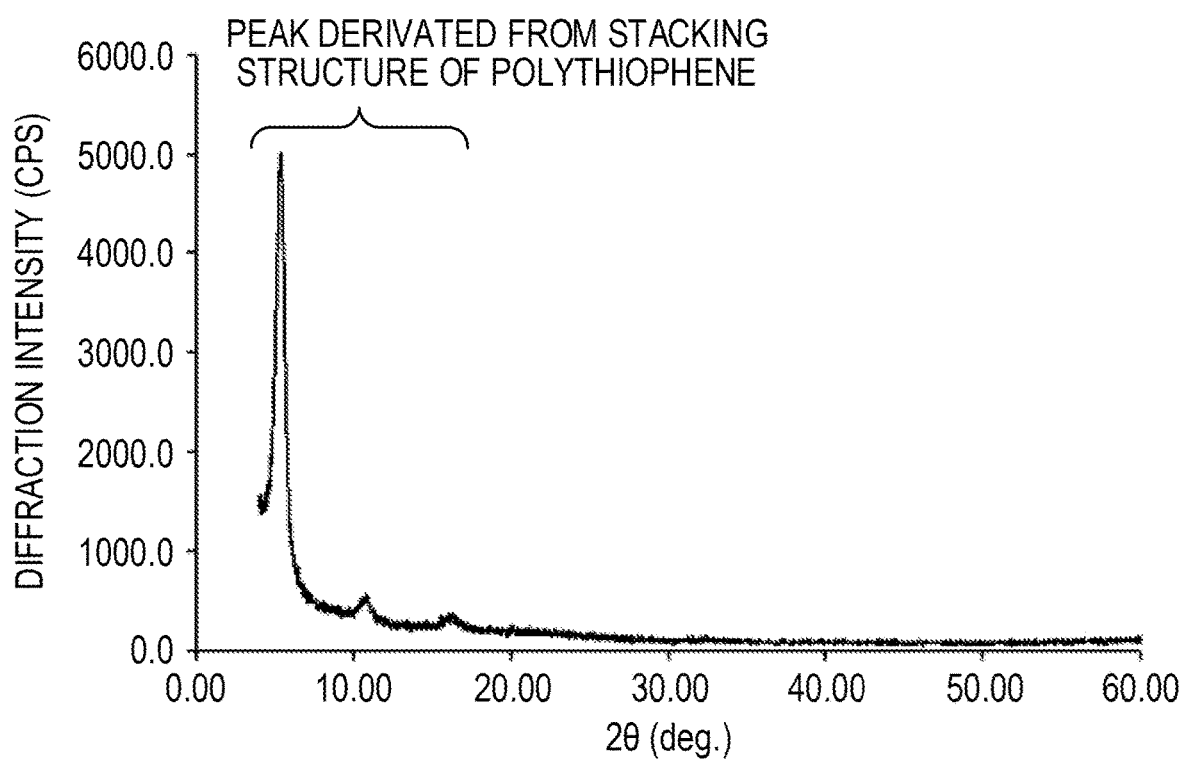
FIG. 11 is an X-ray diffraction profile obtained by measuring the gas sensor device manufactured by the method of manufacturing the gas sensor device according to the first embodiment.

FIG. 11 is an X-ray diffraction profile obtained by measuring the gas sensor device 10 manufactured by the method of manufacturing the gas sensor device according to the first embodiment. As illustrated in FIG. 11, only the peak derived from the stacking structure of P3HT which is the material of the polythiophene film 14 is observed. Since no peak representing cuprous bromide is observed, it is estimated that a cuprous bromide crystal in a size of at least several nm has not been formed.

Figure 12:
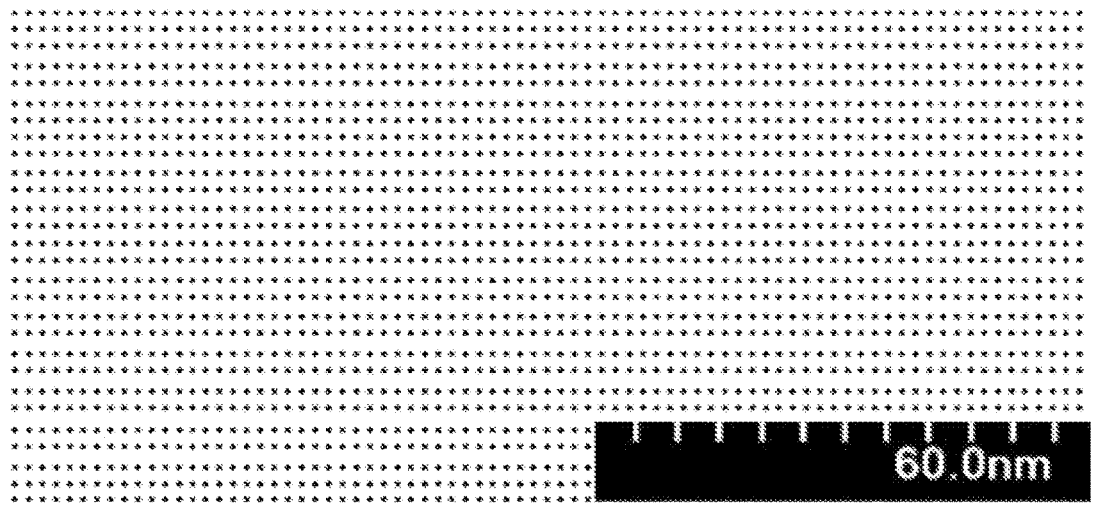
FIG. 12 illustrates an exemplary of a scanning transmission electron microscopic image of the gas sensor device manufactured by the method of manufacturing the gas sensor device according to the first embodiment.

FIG. 12 illustrates an exemplary of a scanning transmission electron microscopic image of the gas sensor device 10 manufactured by the method of manufacturing the gas sensor device according to the first embodiment. FIG. 12 is a schematic view of a scanning transmission electron microscopic image of the gas sensor device 10 manufactured by the method of manufacturing the gas sensor device according to the first embodiment. No crystal structure of cuprous bromide is observed.

From the analysis result, it is estimated that the gas sensor device 10 manufactured by the method of manufacturing the gas sensor device according to the first embodiment mainly contains P3HT which is the material of the polythiophene film 14 and has a structure in which cuprous bromide is discretely present without growing as a crystal, on the surface of P3HT.

Hereinafter, a gas measuring device according to a second embodiment will be described with reference to FIG. 13. The gas measuring device according to the second embodiment detects a detection target gas in a measurement target gas. In the gas measuring device according to the second embodiment, the measurement target gas is, for example, the exhaled breath of a person, and the detection target gas is ammonia gas.

Figure 13:
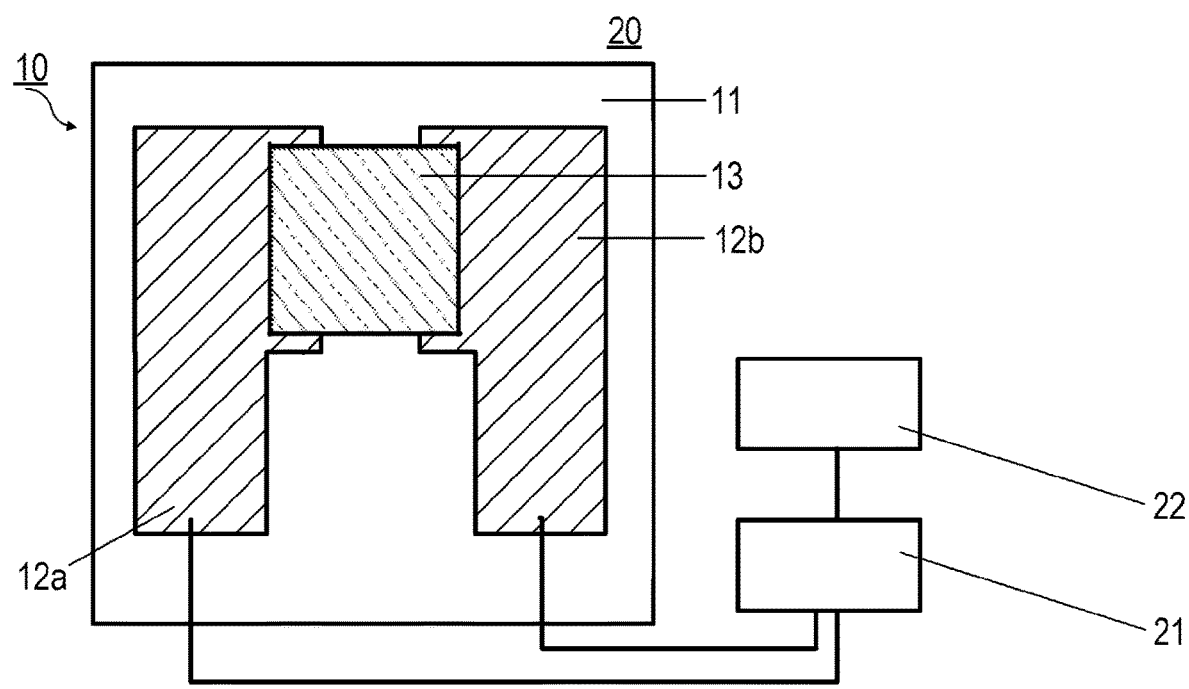
FIG. 13 is a view illustrating a gas measuring device according to a second embodiment.

FIG. 13 is a view illustrating the gas measuring device according to the second embodiment. As illustrated in FIG. 13, the gas measuring device 20 includes the gas sensor device 10 and a measuring circuit including a measurement circuit 21 and a calculation circuit 22.

The measurement circuit 21 is electrically coupled to the two electrodes 12a and 12b of the gas sensor device 10, and measures an electrical characteristic of the contacting portion 13 of the gas sensor device 10. The measurement circuit 21 is a measurement circuit such as, for example, an electrometer. For example, the measurement circuit 21 measures an electric resistance value of the contacting portion 13 by applying a constant potential to both ends of the contacting portion 13 and a resistance which are coupled to each other in a series and measuring a potential of the contact point between the contacting portion 13 and the resistance. Further, the measurement circuit 21 applies a constant potential to both ends of the contacting portion 13 and measures a current value of the contact point in the contact portion.

The calculation circuit 22 calculates a change in the electrical characteristic of the contacting portion 13 of the gas sensor device 10. The calculation circuit 22 is electrically coupled to the measurement circuit 21 and receives the measurement value of the electric characteristic of the gas sensor device 10 which is measured by the measurement circuit 21, to calculate the change of the electric characteristic. The calculation circuit 22 is, for example, a control device such as a computer. The change of the electric characteristic is, for example, a ratio or a difference between the initial electric resistance value $R_O$ of the contacting portion 13 and the electric resistance value R after elapse of a certain time period. In addition, the change of the electric characteristic is, for example, a ratio or a difference between an initial current value of the contacting portion 13 and a current value after elapse of a certain time period. The calculation circuit 22 may calculate the concentration of the detection target gas based on the calculated change of the electric characteristic.

For example, the calculation circuit 22 may record the electric resistance value of the contacting portion 13 which is measured by the measurement circuit 21 once every second, and set the electric resistance value measured before the exposure to the measurement target gas as the initial electric resistance value $R_O$. Then, the calculation circuit 22 may calculate a change of the electric resistance value R per unit time with respect to the initial electric resistance value $R_O$ after elapse of a certain time period (e.g., 10 seconds) from the start of the exposure to the measurement target gas.

The calculation circuit 22 may calculate the concentration of the detection target gas by creating and recording a profile of a change of the electrical characteristic of the contacting portion 13 per unit time, e.g., a change profile of the electric resistance value of the contacting portion 13 per unit time when a detection target gas having a known concentration is exposed to the gas sensor device 10, and by comparing a calculated change of the electric resistance value per unit time and the recorded profile with each other.

The calculation circuit 22 may calculate the concentration of the gas based on a change of the electrical characteristic for a certain time period from a time point when the measurement target gas is exposed to the gas sensor device 10, e.g., a change of the electric resistance value per unit time for a time period until a response to hydrogen sulfur is started.

As described above, the gas measuring device 20 includes the gas sensor device 10, the measurement circuit 21, and the calculation circuit 22, and may perform an accurate quantification of ammonia by including the gas sensor device 10 exhibiting a high ammonia gas selectivity.

Hereinafter, descriptions will be made on the response of the gas measuring device according to the second embodiment to ammonia and hydrogen sulfur each having a concentration of 1 ppm with reference to FIGS. 14 and 15.

The gas sensor device 10 is provided in the air flow, and alternately exposed to the clean air and ammonia having a concentration of 1 ppm, to measure an electric resistance value of the gas sensor device 10 per unit time with respect to the ammonia. Similarly, the gas sensor device 10 is provided in the air flow, and alternately exposed to the dean air and hydrogen sulfide having a concentration of 1 ppm, to measure an electric resistance value of the gas sensor device 10 per unit time with respect to the hydrogen sulfide.

Figure 14:
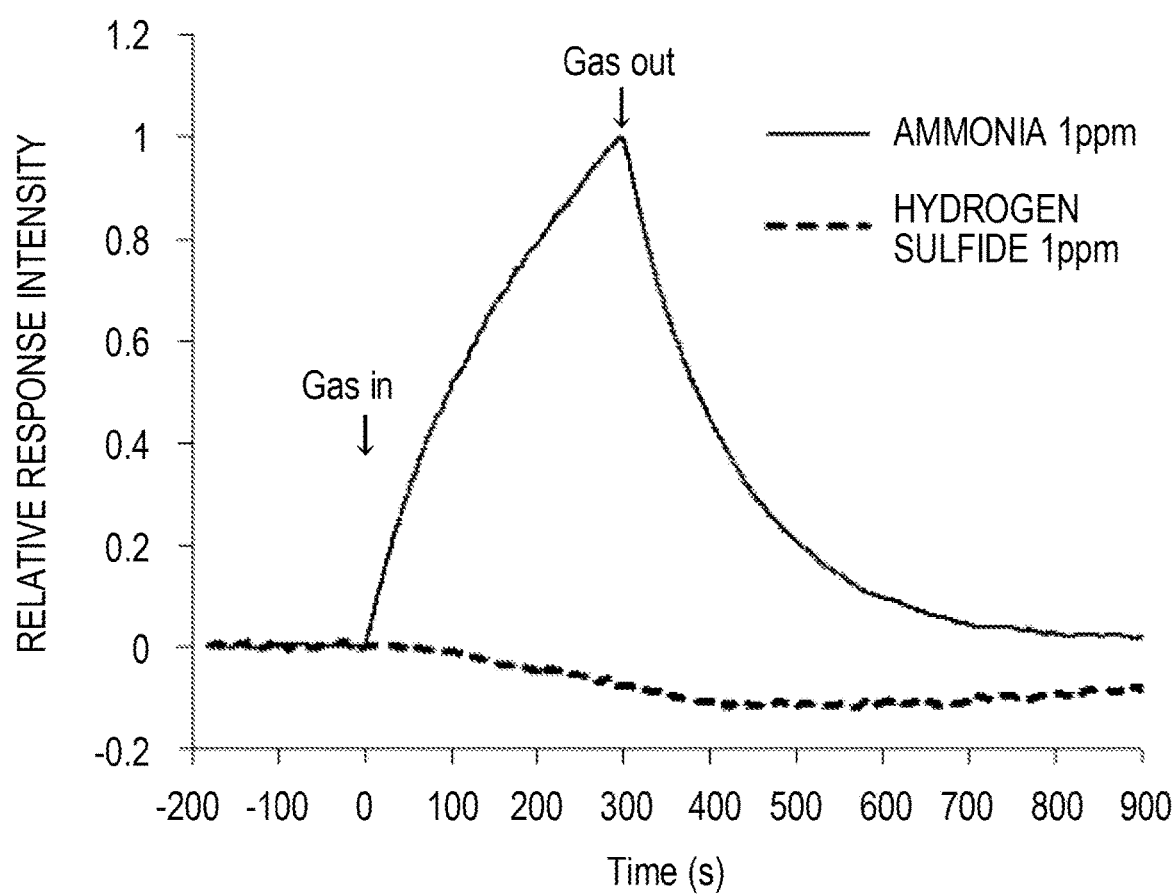
FIG. 14 is a response profile of the gas sensor device according to the second embodiment to ammonia gas and hydrogen sulfide gas each having a concentration of 1 ppm in the air.

FIG. 14 is a profile of a response of the gas sensor device according to the second embodiment with respect to the ammonia gas and the hydrogen sulfide gas each having a concentration of 1 ppm in the air. The horizontal axis represents time, and the vertical axis represents relative response intensity. The relative response intensity refers to a ratio between the initial electrical resistance value $R_O$ of the gas sensor device 10 under the clean air and the electrical resistance value R measured every second. The gas sensor device 10 exhibits the response by the electric resistance value with a high sensitivity with respect to the gas to the extent that the relative response intensity largely changes per unit time.

As Illustrated in FIG. 14, the relative response intensity per unit time largely changes by the contact of the gas sensor device 10 with ammonia. Meanwhile, in the contact of the gas sensor device 10 with hydrogen sulfide, the relative response intensity does not largely change for 300 seconds from a time point when the exposure is started. From the result that the gas sensor device 10 responds to ammonia with a high sensitivity and responds to hydrogen sulfide with a low sensitivity, the gas sensor device 10 exhibits a high ammonia gas selectivity.

Figure 15:
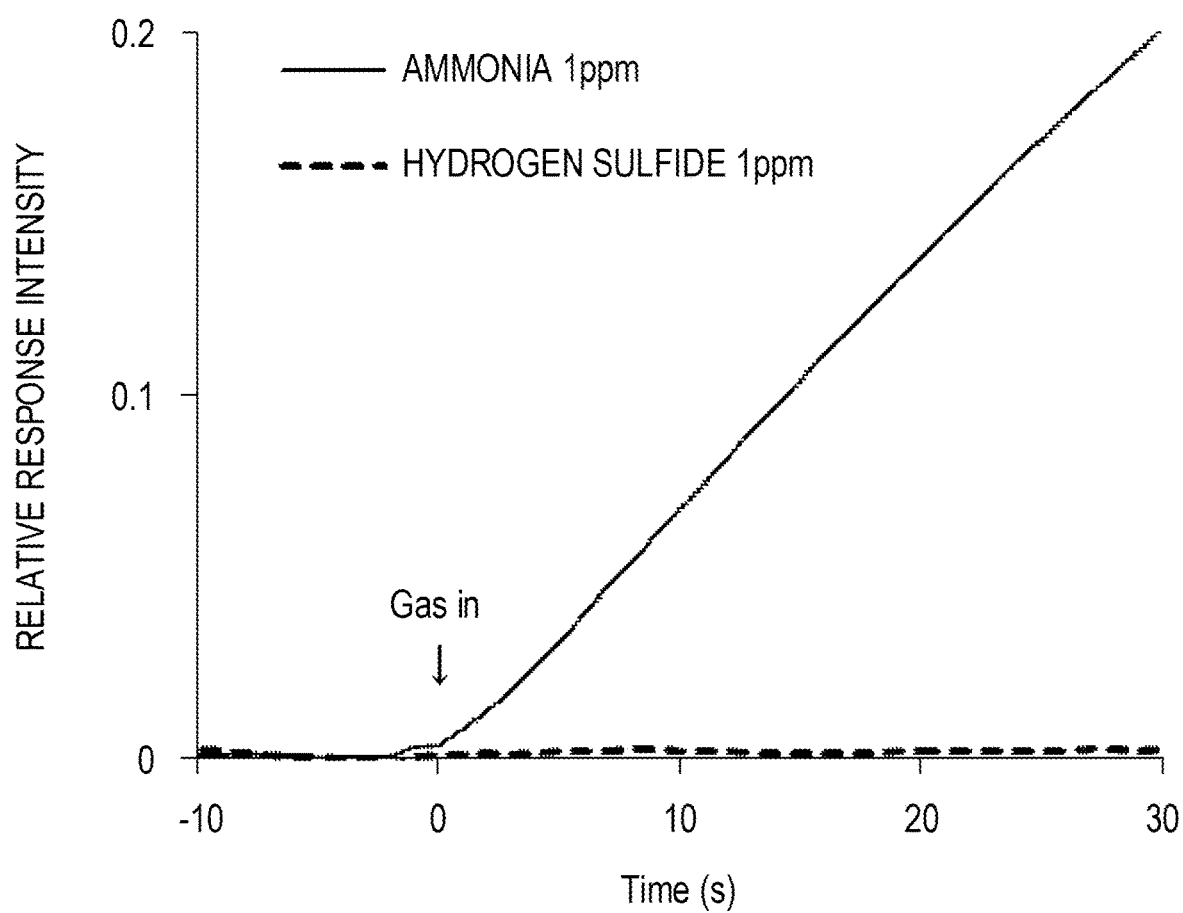
FIG. 15 is an enlarged view illustrating an initial response for 30 seconds from a start of an exposure to a target gas in the response profile illustrated in FIG. 14.

FIG. 15 is an enlarged view illustrating the initial response for 30 seconds from the start of the exposure to the target gas in the response profile illustrated FIG. 14. As illustrated in FIG. 15, the response of the gas sensor device 10 with respect to hydrogen sulfide exhibits no significant change in the relative response intensity for 30 seconds from the time point when the exposure is started. This is because the formation of the coordination bond between the hydrogen sulfide and the cuprous bromide is hindered by the coordination bond between the polythiophene and the cuprous bromide, and thus, the start of the response of the gas sensor device 10 by the electric resistance value to the hydrogen sulfide is delayed.

From the phenomenon that the start of the response of the gas sensor device 10 to the hydrogen sulfide is delayed, an accurate quantification of ammonia may be performed without being affected by the hydrogen sulfide, by using the electric resistance value, as quantification, for a time period from the start of the exposure to the measurement target gas until the start of the response to the hydrogen sulfide. This is obvious because the start of the response of the gas sensor device 10 to the hydrogen sulfide is delayed, as compared with a comparative example to be described later.

Hereinafter, an exhaled gas measuring device according to a third embodiment will be described with reference to FIG. 16. The exhaled gas measuring device according to the third embodiment detects ammonia gas in the exhaled breath of a person. The ammonia gas contained in the exhaled breath is known as a marker gas indicating *pylori* bacterium infection related to a stomach cancer and a heart disease. A simple examination for early detecting diseases such as cancers may be performed by using the exhaled gas measuring device according to the third embodiment.

Figure 16:
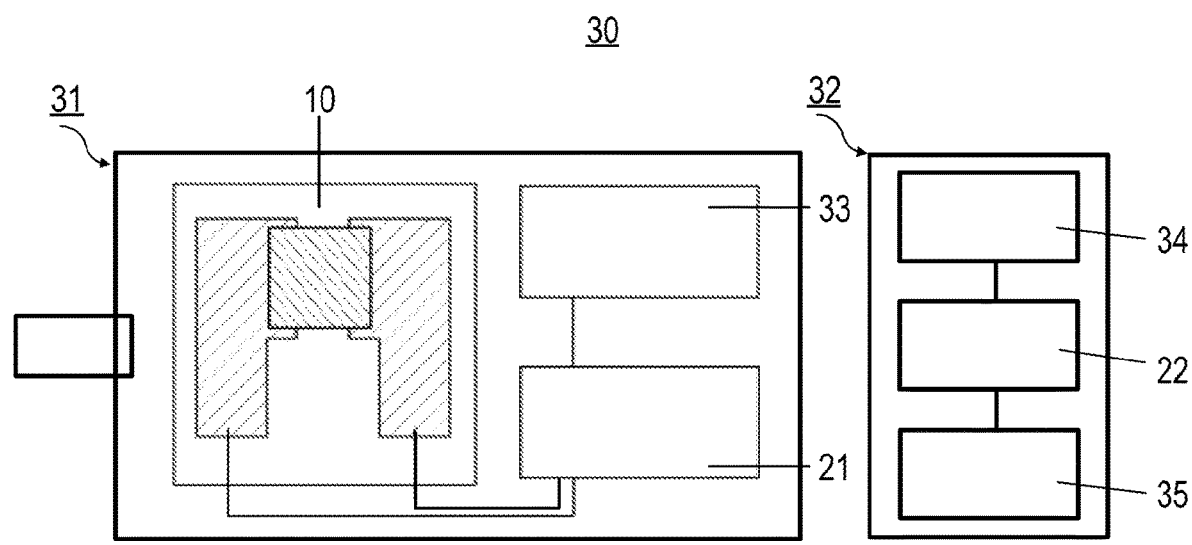
FIG. 16 is a view illustrating an exhaled breath measuring device according to a third embodiment.

FIG. 16 is a view illustrating the exhaled gas measuring device according to the third embodiment. As illustrated in FIG. 16, the exhaled gas measuring device 30 includes a sensor 31 having the gas sensor device 10, the measurement circuit 21, and a transmission circuit 33, and a monitor having a reception circuit 34, the calculation circuit 22, and an output circuit 35.

The sensor 31 is a housing accommodating the gas sensor device 10 and has a blow-in port and an exhaust port such that the exhaled breath exposed to the gas sensor device 10 may be introduced into the sensor 31. The sensor 31 may have, for example, a sensor for measuring a temperature, humidity, and an atmospheric pressure, or another gas sensor device for detecting a gas other than ammonia gas as a detection target gas.

A person to be measured blows his/her exhaled breath into the housing of the sensor 31 through the blow-in port for a certain time period from a starting time of the measurement. The time for blowing the exhaled breath into the sensor 31 is, for example, 15 seconds.

The transmission circuit 33 transmits the electrical characteristic of the gas sensor device 10 which is measured by the measurement circuit 21 from the starting time of the measurement, once per second to the monitor 32 having the reception circuit 34 via a wireless communication.

The calculation circuit 22 calculates the electrical characteristic for a certain time period such as, for example, a change in the electrical resistance value of the contacting portion 13 of the gas sensor device 10 per unit time for a time period from 4 to 13 seconds after the starting time of the measurement. Based on the calculated change of the electric resistance value per unit time, the calculation circuit 22 calculates the concentration of the ammonia gas and obtains the concentration as a calculation result. The calculation circuit 22 may save a calibration curve which is created in advance and represents a change of the electric resistance value of the gas sensor device 10 in response to a concentration of the ammonia gas, and calculate a concentration of the ammonia gas by comparing the calculated change of the electric resistance value per unit time with the calibration curve.

The output circuit 35 outputs the calculation result obtained by the calculation circuit 22. The output circuit 35 is, for example, a display or a speaker.

As described above, the exhaled gas measuring device includes the sensor 31 having the gas sensor device 10, the measurement circuit 21, and the transmission circuit 33, and the monitor 32 having the reception circuit 34, the calculation circuit 22, and the output circuit 35, and may accurately and easily measure the concentration of the ammonia gas in the exhaled gas.

Hereinafter, a gas sensor device according to a comparative example will be described. Descriptions of similar components to those in the first embodiment will be omitted.

The gas sensor device according to the comparative example includes a contacting portion of cuprous bromide, instead of the contacting portion of the first embodiment which is the polythiophene film with cuprous bromide adsorbed thereto.

Hereinafter, an operation principle of the gas sensor device according to the comparative example will be described.

When the detection target gas, ammonia, comes into contact with the contacting portion 13, the ammonia donates an electron to the cuprous bromide so as to form a coordination bond. When the electron is donated from the ammonia to the cuprous bromide, the concentration of the p-type carrier in the cuprous bromide decreases, and thus, the electric resistance value of the contacting portion 13 decreases.

Hereinafter, descriptions will be made on the response of the gas sensor device of the comparative example by the change of the electric resistance value to ammonia and hydrogen sulfide each having a concentration of 1 ppm, with reference to FIGS. 17 and 18. The change of the electric resistance value of the gas sensor device according to the comparative example will be measured per time by using the similar method to that used for the gas measuring device according to the second embodiment.

Figure 17:
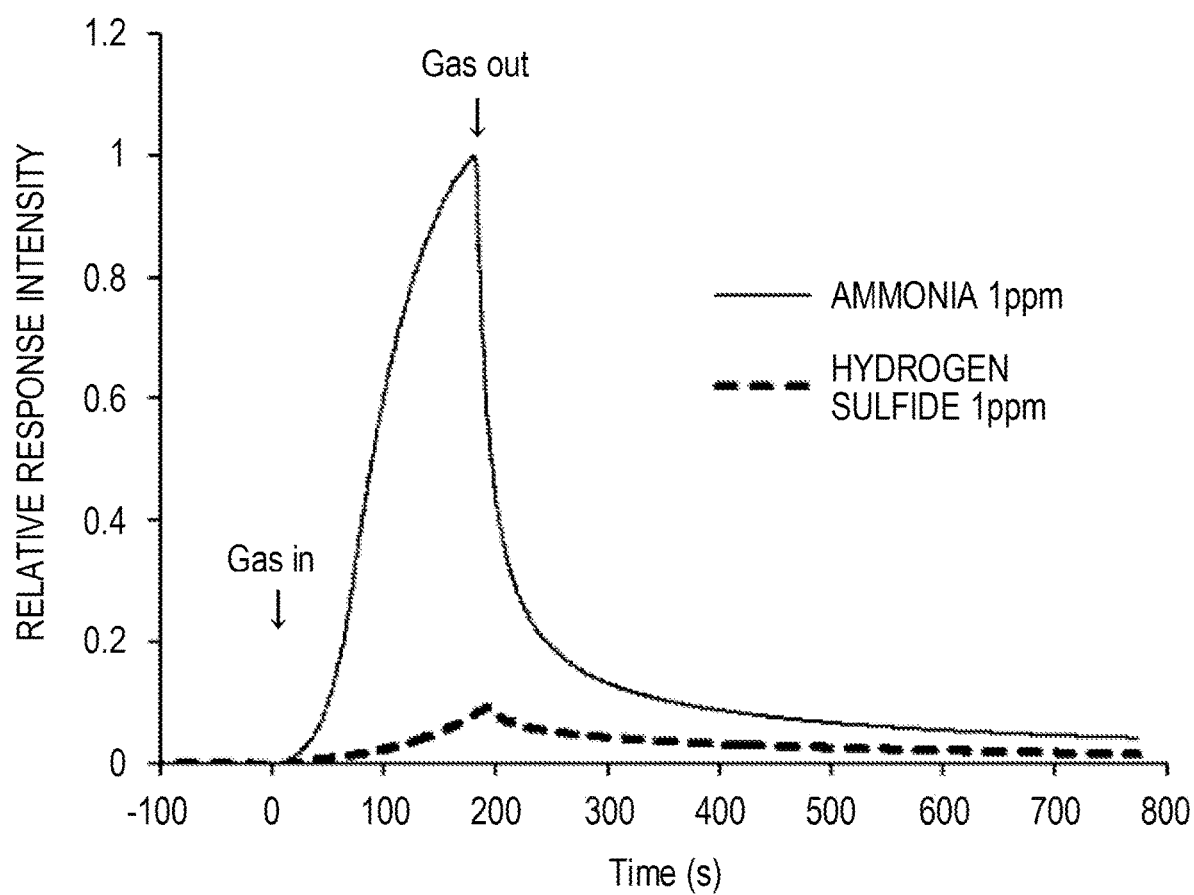
FIG. 17 is a response profile of a gas sensor device according to a comparative example to ammonia gas and hydrogen sulfide gas each having a concentration of 1 ppm in the air.
Figure 18:
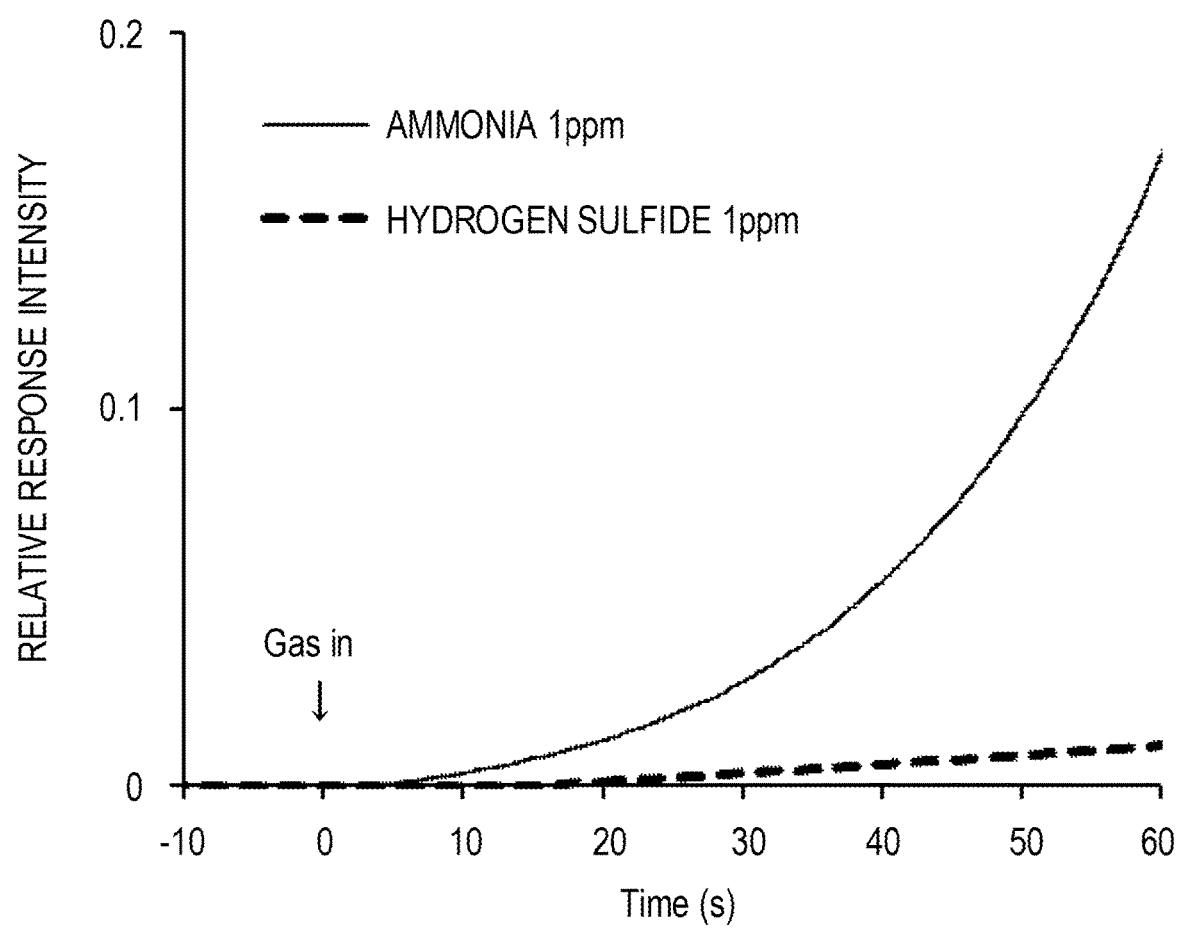
FIG. 18 is an enlarged view illustrating an initial response for 60 seconds from a start of an exposure to a target gas, in the response profile illustrated in FIG. 17.

FIG. 17 is a response profile of the gas sensor device according to the comparative example with respect to the ammonia gas and the hydrogen sulfide gas each having a concentration of 1 ppm in the air. FIG. 18 is an enlarged view illustrating the initial response for 60 seconds from the start of the exposure to the target gas in the response profile illustrated in FIG. 17. The response intensity of the gas sensor device 10 to hydrogen sulfide increases at a rate of about 1/10 of the response to ammonia. The start of the response of the gas sensor device 10 to hydrogen sulfide is concurrent with the start of the response to ammonia.

Hereinafter, a method of manufacturing the gas sensor device according to the comparative example will be described. Descriptions of similar portions to those in the first embodiment will be omitted.

In the method of manufacturing the gas sensor device according to the comparative example, a copper film is formed to be electrically coupled to the first and second electrodes, instead of forming the polythiophene film in the first embodiment, and cupric bromide is brought into contact with the copper film so as to form the contacting portion of cuprous bromide.

Instead of the polythiophene film 14 of the first embodiment, a copper film having a side of 5 mm and a film thickness of 60 nm is formed by using a mask at the position electrically coupled to the two electrodes 12*a* and 12*b* on the substrate 11 of the gas sensor device 10 in FIG. 8.

A cupric bromide solution is brought into contact with the formed copper film. The cupric bromide solution is washed out with pure methanol after 0.1 mol/L of an aqueous solution is dropped and immersion is performed for one minute.

Instead of the contacting portion 13 of the first embodiment which is the polythiophene film 14 with cuprous bromide adsorbed thereto in FIG. 10, the contacting portion 13 of cuprous bromide is formed so that the gas sensor device 10 is manufactured.

The gas detecting method by the gas sensor device and the gas measuring device according to the embodiments of the present disclosure is merely an example, and an optimum method may be selected depending on a detection target gas or an environment condition to be used.

Figure 19:
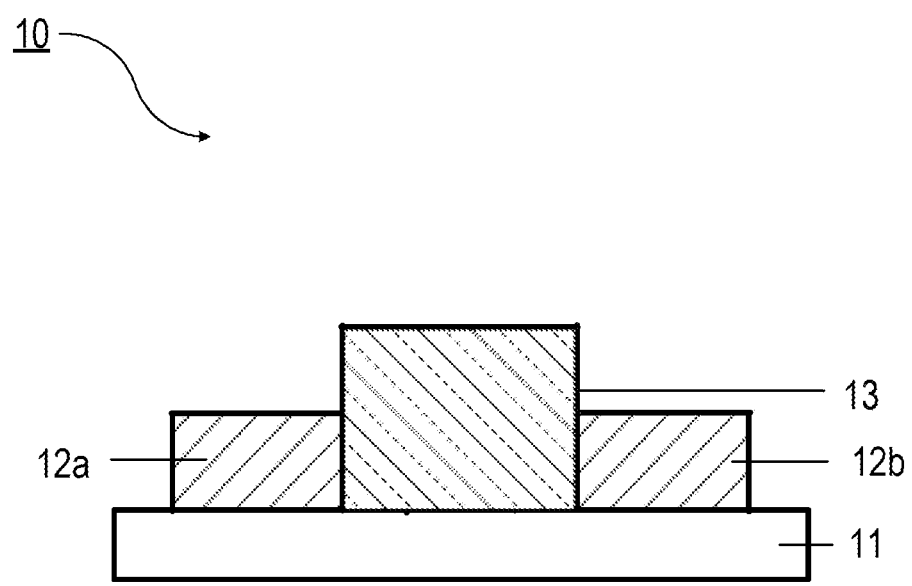
FIG. 19 is a view illustrating a modification of the gas sensor device according to the first embodiment.

FIG. 19 is a view illustrating a modification of the gas sensor device according to the first embodiment. For example, the contacting portion 13 may be formed in contact with only the lateral surfaces of the two electrodes 12*a* and 12*b* as illustrated in FIG. 19.

Figure 20:
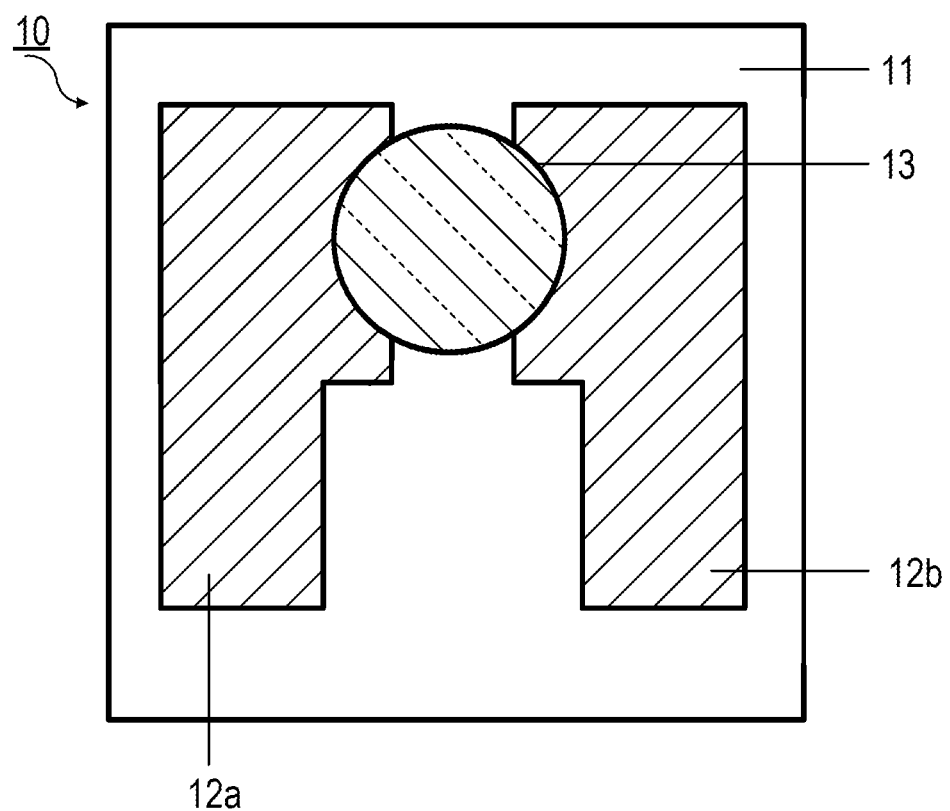
FIG. 20 is a view illustrating another modification of the gas sensor device according to the first embodiment.

FIG. 20 is a view illustrating a modification of the gas sensor device according to the first embodiment. The contacting portion 13 may have any shape as long as the contacting portion 13 is electrically coupled to the two electrodes 12*a* and 12*b*. For example, the contacting portion 13 may have a circular shape as illustrated in FIG. 20.

The polythiophene film in the first embodiment may be formed of a single polythiophene molecule.

All examples and conditional language recited herein are intended for pedagogical purposes to aid the reader in understanding the disclosure and the concepts contributed by the inventor to furthering the art, and are to be construed as being without limitation to such specifically recited examples and conditions, nor does the organization of such examples in the specification relate to a showing of the superiority and inferiority of the disclosure. Although the embodiment(s) of the present disclosure has (have) been described in detail, it should be understood that the various changes, substitutions, and alterations could be made hereto without departing from the spirit and scope of the disclosure.

What is claimed is:

1. A method of manufacturing a gas sensor device, the method comprising:
    forming a first electrode and a second electrode on a substrate;
    forming a polythiophene film on the substrate between the first and second electrodes to be electrically coupled to the first and second electrodes by applying a solution which is obtained by dissolving polythiophene in organic solvent into the substrate and performing a first drying;
    bringing a cupric bromide into contact with the polythiophene film by contacting the polythiophene film and the cupric bromide; and
    forming the polythiophene film absorbed the cuprous bromide,
    the contacting the polythiophene film and the cupric bromide is performed by dropping a solution of the cupric bromide into the polythiophene film, washing the polythiophene film after a specific period of time elapses and performing a second drying.

2. The method of manufacturing a gas sensor device according to claim 1, wherein the solution is applied into a rectangular shape having a side of a specific length.

* * * * *